United States Patent [19]

Mori

[11] Patent Number: 5,567,557
[45] Date of Patent: Oct. 22, 1996

[54] ELECTROPHOTOGRAPHIC PHOTORECEPTOR

[75] Inventor: Nobuyoshi Mori, Nagano, Japan

[73] Assignee: Fuji Electric Co., Kawasaki, Japan

[21] Appl. No.: 393,411

[22] Filed: Feb. 23, 1995

[30] Foreign Application Priority Data

Feb. 23, 1994 [JP] Japan ................................ 6-024634

[51] Int. Cl.$^6$ ..................................................... G03G 5/147
[52] U.S. Cl. ............................................. 430/58; 430/132
[58] Field of Search ................................. 430/66, 67, 58, 430/59, 132

[56] References Cited

U.S. PATENT DOCUMENTS

| | | | |
|---|---|---|---|
| 4,207,229 | 6/1980 | Spivack | 260/926 |
| 5,008,168 | 4/1991 | Nakagawa et al. | 430/56 |
| 5,192,633 | 3/1993 | Iwasaki et al. | 430/59 |

FOREIGN PATENT DOCUMENTS

| | | |
|---|---|---|
| 3625766 | 2/1987 | Germany. |
| 62-105151 | 5/1987 | Japan. |
| 62-234164 | 10/1987 | Japan. |
| 1118137 | 10/1989 | Japan. |
| 5257299 | 10/1993 | Japan. |
| 2180659 | 7/1985 | United Kingdom. |
| 2201255 | 7/1987 | United Kingdom. |

*Primary Examiner*—John Goodrow
*Attorney, Agent, or Firm*—Morrison Law Firm

[57] ABSTRACT

An electrophotographic photoreceptor consists of an intermediate layer on a conductive substrate. A photosensitive bilayer is coated on the intermediate layer. The outermost layer if the photosensitive bilayer contains a combination of an ester phosphite antioxidant and a hindered phenol antioxidant. This organic photoreceptor has improved resistance to performance degradation and degradation in repetition characteristics from exposure to active gases (such as ozone). A method of producing the electrophotographic photoreceptor according to the invention is also taught.

9 Claims, 1 Drawing Sheet

ELECTROPHOTOGRAPHIC PHOTORECEPTOR

BACKGROUND OF THE INVENTION

The present invention relates to electrophotographic photoreceptors. More particularly, the present invention relates to an organic electrophotographic photoreceptor having improved durability against active gases (such as ozone), as well as enhanced photoreception and repetition characteristics.

Among conventional devices, electrophotographic photoreceptors (referred to as "photoreceptors" below) are generally used in such applications as copiers and printers. These known uses for photoreceptors feature devices which consist mainly of an inorganic photoconductive material such as selenium, selenium alloy, zinc sulfide, or cadmium sulfide.

Many photoreceptors of organic photoconductive material have recently been developed having advantageous characteristics. These organic photoconductive materials capitalize upon improved properties including flexibility, heat stability, film formation capability, light weight, and low costs.

Prominent among organic photoconductive materials are function-separated laminated organic photoreceptors. Generally speaking these materials include a photosensitive layer which is divided into a charge generation layer (for receiving light to generate charge carriers) and a charge transport layer (for transporting charge carriers generated).

Function-separated laminated organic photoreceptors additionally provide improved characteristics when the respective layers are formed of an material suitable for corresponding functions and combined. Such photoreceptors may be combined, for example in a negatively-charged function-separated laminated organic photoreceptor. This type of function-separated laminated organic photoreceptor generally includes a charge generation layer and a charge transport layer laminated on a conductive substrate. The layers are arranged in this particular order for generating a photosensitivity comparable to that of selenium photoreceptors.

Electrophotographic devices are used for image formation processes, which are repeatedly performed upon their surfaces. Cycles of these image formation processes include charging, exposure, development, transfer, cleaning, and erasing. Since these image formation processes must be repeatedly done on the surface of photoreceptors, the photoreceptors must exhibit high levels of stability. This stability is required to last over time throughout repeated cycles of the image formation processes, numbering in the thousands.

Prior art photoreceptors have sought improved productivity, for operation over repeated cycles. However, prior art photoreceptors have failed to provide high quality images during repetitive processes. Consequently, the overall quality of the reproduced image steadily declined over the time with known devices.

It is further noted that repetitive processes such as those outlined above cause degradation of the charge potential which substantially increases the residual potential, resulting in inferior images.

The decrease in the overall quality is attributed to numerous factors. A primary factor is corona discharge. When photoreceptors are used in photocopying machines, they repeatedly contact noxious gases, such as ozone, generated by corona discharge.

Ozone gas in particular has been implicated in adversely effecting the function of photoreceptors in photocopying machines. $NO_x$ is another gas which has been implicated in detrimentally impacting overall quality and life span of conventional photoreceptors used in photocopying machines.

In recent years there has been a growing demand for photoreceptors which provide faithful reproductions without compromising the quality of the image. Demand has also fueled an interest in photoreceptors which are capable of providing high quality images at minimal cost and that retain their imaging properties over time and repeated use.

It is also required that the particular photoreceptors exhibit improved electric characteristics, showing stability in respective decreases in charge potentials. In general, charge generation layers absorb light and generate pairs of charge carriers. Such generated charge carriers must then be transported quickly and injected into conductive substrates or into a charge transport layer. This process must be accomplished quickly before the charge carriers are lost to recombination or charge traps.

It thus is preferable that the charge generation layer have adequate thinness and an even and consistent width. Conventional photoreceptors have a charge generation layers measuring less than one μm. However, prior art photoreceptors with thin film charge generating layers are plagued with numerous disadvantages.

Prior art disclosures include the addition of various photodeterioration agents to prevent deleterious changes in surface potential. Use of various antioxidants (for example, tri-akylphenol derivatives or di-lauryl thiopropionates) is known in prior art photosensitive layers. Other organic phosphites have been added for reducing or preventing degradation of prior art photosensitive layers.

Attention is called to the following publications which suggest the use of specific compounds in order combat degradation of conventional photosensitive layers. These publications include, Japanese Laid Open Patent Publication No. 62-234164, Japanese Laid Open Patent Publication No. 62-105151, Japanese Laid Open Patent Publication No. 1-118137, and Japanese Laid Open Patent Publication No. 5-257299.

Japanese Laid Open Patent Publication No. 62-234164 teaches the use of an organic phosphite compound which is incorporated into either the charge generating or charge transfer layer. However, this disclosure is innocently silent of any disclosure suggesting the use of a hindered phenol in combination with an antioxidant as used in the present invention.

Similarly, Japanese Laid Open Patent Publication No. 62-105151, Japanese Laid Open Patent Publication No. 1-118137, and Japanese Laid Open Patent Publication No. 5-257299 envision using various conventional inorganic compounds incorporated within photosensitive layers for preventing changes in surface stability of the photoreceptors.

Japanese Laid Open Patent Publication No. 1-118137 suggests using a polycarbonate in conjunction with conventional hindered phenols in order to maintain consistent electrical characteristics. This disclosure, however, is devoid of teachings incorporating an antioxidant as used in the present invention.

Likewise, Japanese Laid Open Patent Publication No. 5-257299 proposes using additional binder resins made of specified copolymers in order to adjust the electrical resistance and to resist mechanical changes in, the photosensitive layer. However, as among other conventional disclosures, the conventional binder component is combined with known hindered phenols or amines. Consequently, the benefits of combining an ester phosphite antioxidant and a hindered phenol antioxidant, as taught by the present invention, are not procured.

Unfortunately, as discussed above, of prime concern with organic photoreceptors are the charge potentials which are reduced during repetitive use. This causes degradation of charging characteristics, resulting in degraded image quality for images produced with such photoreceptors. Degradation of such charging characteristics is mainly due to the degradation of organic material on the surface of photoreceptors caused by active gases, such as ozone ($O_3$). These active gases are generated by corona discharge from a charger, and continue to provide a problem among known disclosures.

In other prior art attempts to solve this problem, fans have been installed for ventilating the ozone. The fans remove ozone to reduce the amount of ozone contacting surfaces of photoreceptors.

Alternatively, various antioxidants such as 2,6-di-butyl-4-methylphenol (BHT), pentaerythritol-tetrakis[3-(3,5-di-t-butyl-4-hydroxyphenyl)propionate], 2,4-bis-(n-octylthio)-6-(4-hydroxy-3,5-di-t-butylanilino)-1,3,5-triazine have been added to outermost surfaces of photoreceptors to prevent such degradation.

However, neither employing such conventional ventilation means, nor use of antioxidants has sufficiently protected photoreceptor surfaces from ozone driven effects. To date, nothing known among the prior art has adequately addressed this longstanding problem of degradation of charging characteristics. Fan-equipped devices have proven to be prohibitively expensive and addition of an antioxidants likewise is problematic.

Thus a clear need exists to prevent active gases from adversely affecting surfaces of photoreceptors and causing such photoreceptors to have degraded charging characteristics. In addition, known organic photoreceptors still have not managed to satisfy the market's requirements for repetition characteristics.

OBJECTS AND SUMMARY OF THE INVENTION

Accordingly it is an object of the present invention to provide an organic photoreceptor which overcomes the drawbacks of the prior art.

It is further object of the invention to provide an organic photoreceptor having improved durability against active gases such as ozone ($O_3$).

It is still a further object of the invention to provide an organic photoreceptor having enhanced repetition characteristics.

It is yet a still further object of the invention to provide an organic photoreceptor exhibiting high levels of image formation capability over time.

Briefly stated, the present invention provides an electrophotographic photoreceptor consisting of a photosensitive bilayer on a conductive substrate wherein the outermost sublayer contains an ester phosphite antioxidant and a hindered phenol antioxidant. This organic photoreceptor has improved durability against active gases (such as ozone) and enhanced repetition characteristics. A method of producing same is also taught.

According to a feature of the of the invention, there is provided an electrophotgraphic photoreceptor which comprises; a conductive substrate, an intermediate layer on the conductive substrate, a photosensitive bilayer of an organic material on the intermediate layer, the photosensitive bilayer includes a charge generation layer and a charge transport layer, the charge generation layer being deposited on the intermediate layer, the charge transport layer being deposited on the charge generation layer, the charge transport layer being an outermost layer of the photosensitive bilayer, and the charge transport layer contains an ester phosphite antioxidant and a hindered phenol antioxidant.

According to a further feature of the invention, there is provided an electrophotgraphic photoreceptor which comprises; a conductive substrate, an intermediate layer on the substrate, a photosensitive bilayer of an organic material on the intermediate layer, an outermost layer of said photosensitive bilayer contains an ester phosphite antioxidant and a hindered phenol antioxidant,and the ester phosphite antioxidant is a compound represented by a following general chemical formula:

$$[A\!-\!O]_3P \tag{1}$$

Wherein:

A represents a phenyl group that may have a substituent.

According to another feature of the invention, there is provided an electrophotographic photoreceptor which comprises; a conductive substrate, an intermediate layer on the substrate, a photosensitive bilayer of an organic material on the intermediate layer, an outermost layer of said photosensitive bilayer contains an ester phosphite antioxidant and a hindered phenol antioxidant, and the ester phosphite antioxidant is a compound represented by a following general chemical formula:

$$[A\!-\!O]_2P\!-\!O\!-\!R_1 \tag{2}$$

Wherein,

A represents a phenyl group that may have a substituent; and, $R_1$ represents an alkyl group with four carbon atoms or more.

According to yet a further feature of the invention, there is provided an electrophotographic photoreceptor which comprises; a conductive substrate, an intermediate layer on the substrate, a photosensitive bilayer of an organic material on the intermediate layer, an outermost layer of said photosensitive bilayer contains an ester phosphite antioxidant and a hindered phenol antioxidant, and the ester phosphite antioxidant is at least one compound selected from the group represented by the following general chemical formulas:

$$[A\!-\!O]_2P\!-\!O\!-\!R_1 \tag{2}$$

Wherein,

A represents a phenyl group that may have a substituent; and, $R_1$ represents an alkyl group with four carbon atoms or more.

$$R_1\!-\!O\!-\!\underset{\underset{O-R_3}{|}}{P}\!-\!O\!-\!R_2 \tag{3}$$

Wherein:

$R_1$, $R_2$, and $R_3$ each represent an alkyl group with four carbon atoms or more.

According to yet a still further feature of the invention, there is provided a method for producing an electrophotographic photoreceptor comprising; coating an intermediate layer on a conductive substrate, coating a charge generation layer on said intermediate layer, preparing a solution containing a hindered phenol and an ester phosphite antioxidant, and coating said solution on said charge generation layer to form a charge transport layer.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
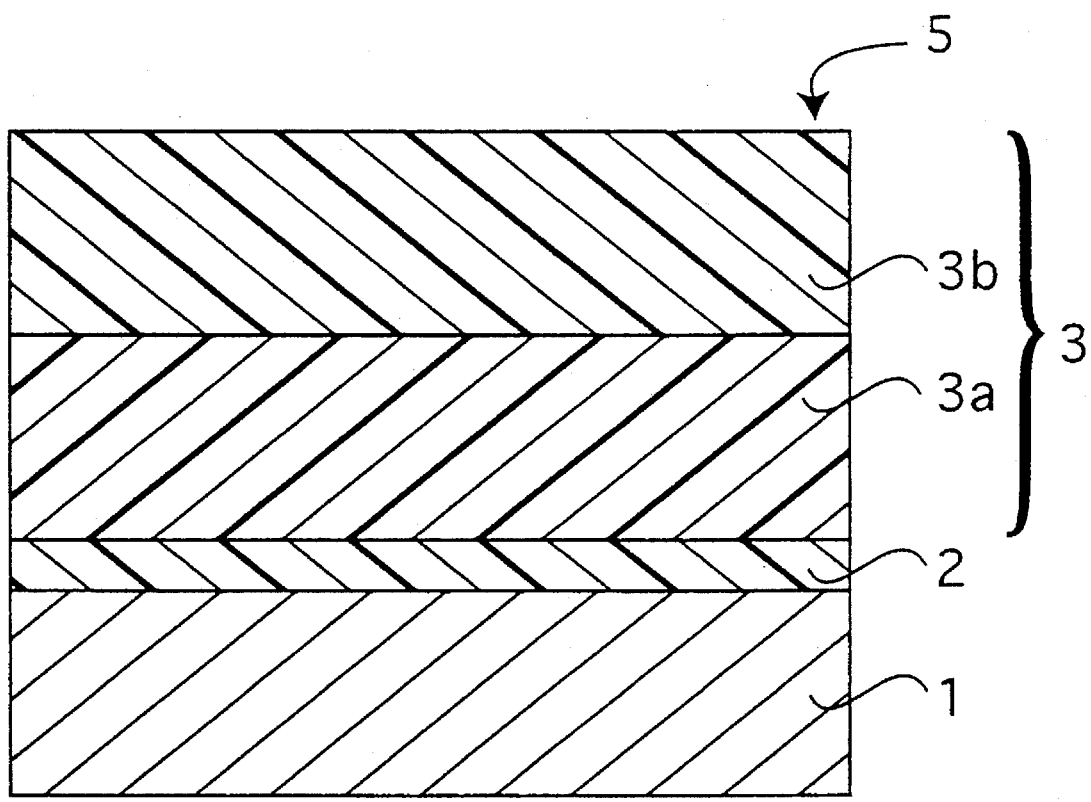
FIG. 1 is a cross-section of an embodiment of a photoreceptor according to the present invention.

The present inventors have discovered that photoreceptors, including photosensitive bilayers of an organic material on a conductive substrate, can decrease the effects of active gases and display enhanced repetition characteristics. Such photoreceptors can be obtained when an outermost sublayer of the photosensitive bilayer contains a combination of an ester phosphite antioxidant and a hindered phenol antioxidant.

For the purposes of this application, the "pts. wt." designation in the embodiments described below refers to pans by weight. "Wt. %" is also used herein to designate atomic weight percentage.

Referring now to FIG. 1, a electrophotographic photoreceptor, shown generally at 5, includes a photosensitive bilayer 3 having a charge generation layer 3a and a charge transport layer 3b. The charge generation layer 3a is laminated on an intermediate layer 2 formed on a conductive substrate 1.

The conductive substrate 1 may be formed in any convenient shape. For example, it may be formed in the shape of a plate, a sheet, a belt, or a cylinder. The material of the conductive substrate 1 may consist of any convenient material such as, for examle aluminum, aluminum alloy, or copper. It may similarly consist of a metal or a plastic coated with aluminum, aluminum alloy, or tin oxide. Coating may be performed by any convenient method such as, for example, vacuum evaporation or sputtering.

The conductive substrate 1 may also be made up of metals, glass or plastics coated with a plating consisting of a mixture of a conductive material and an adequate binding resin. Alternately conductive substrate 1 may consist of plastics containing conductive materials.

Adhesion between the conductive substrate 1 and the photosensitive bilayer 3 is improved by the presence of intermediate layer 2. The intermediate layer 2 also improves control of the injection of charge carriers from the conductive substrate 1 into the photosensitive bilayer 3.

The intermediate layer 2 may consist of polyvinyl alcohol, polyvinyl. methylether, polyamide, polyurethane, melamine resin, phenol resin, or aluminum oxide. The film thickness of this layer preferably ranges from about 0.05 to 20 μm, and more preferably from about 0.05 to 10 μm. The charge generation layer 3a is formed by vapor-evaporating or sputtering phthalocyanine, perylene, bisazo, polycyclic quinone, or indigo pigment. This layer may also be formed using a dye such as squaraine or azulenium. Alternatively, the charge generation layer 3a is made by coating a plating with one of the above-described pigments or dyes dispersed in a solution of binding resin. The solution is evaporated to leave the charge generation layer 3a. These binding resins may include polyvinylbutyral resin, polyallylate resin, polyester resin, or epoxy resin. The film thickness of the charge generation layer is preferably from about 0.1 to 1 μm.

In addition to a charge transport material and a binding resin, the charge transport layer 3b also contains an ester phosphite antioxidant and a hindered phenol antioxidant. The charge transport material further includes conventionally known compounds which are derivatives of hydrazone, hydrazine, triarylamine, styrylamine, indole, induline, butadiene, or pyrazole.

The binding resin includes resins such as polyvinylbutyral, styrene, polycarbonate, polyester, epoxy, urethane, and acrylic.

The charge transport layer 3b preferably contains from about 30 to about 70 wt. % of charge transport material relative to the total solid quantity of this layer. The film thickness of the charge transport layer is preferably 10 to 50 μm, and more preferably 15 to 40 μm.

The charge transport layer 3b preferably contains from about 0.001 to 10 wt. %, and more preferably 0.01 to 5 wt. % of ester phosphite antioxidant relative to the total solid quantity of this layer. In addition, the charge transport layer preferably contains about 0.01 to 10 wt. %, and more preferably 0.1 to 5 wt. % of hindered phenol antioxidant relative to the total solid quantity of this layer.

Various additives may be added to the photoreceptive layer of this invention to improve film formation capability, light fastness, mechanical strength, and potential stability.

EMBODIMENT 1

A 30 mm×30 mm×1 mm aluminum plate was prepared as a conductive substrate. Eight pts. wt. of copolymerized polyamide resin (manufactured by Daicel Hules; trade name "Diamid T-17") was dissolved in a solvent including a mixture of 70 pts. wt. of methanol and 30 pts. wt. of n-butanol. The resulting solution was then coated on the substrate, which was dried at 90 degrees C. for 20 minutes to form an intermediate layer 0.5 μm in film thickness.

Subsequently, 10 pts. wt. of disazo pigment was used as a charge generation material and represented by a following structural formula:

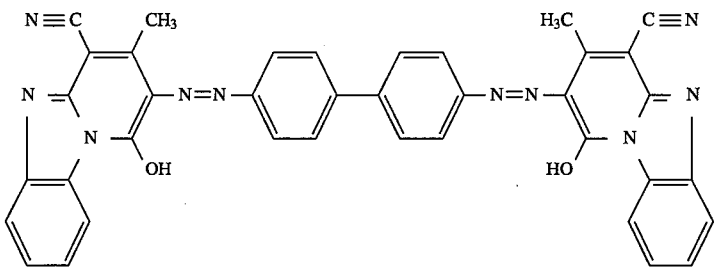

Then, 10 pts. wt. of polyvinylbutyral resin (manufactured by Sekisui Kagaku Co., Ltd.; trade name "S-Lec BH-S"), and 100 pts. wt. of cyclohexane were mixed, and a sand grinder with glass beads 1 mm in diameter was used to disperse the mixture for eight hours. Five hundred pts. wt. of tetrahydrofuran was added to the dispersed liquid to dilute the liquid. The liquid was then coated on the intermediate layer, which was then dried at 90 degrees C. for 20 minutes to form a charge generation layer 0.3 μm in thickness.

Subsequently, the compound denoted by formula 1–3, (below in EXAMPLES section) that is, (2,4-di-t-butylphenol)phosphite used as an ester phosphite antioxidant and the compound 4–1, (below in EXAMPLES section) that is, 2,4-bis-(n-octylthio)-6-(4-hydroxy-3,5-di-t-butylaniline)-1, 3,5-triazine used as a hindered phenol antioxidant were added to 10 pts. wt. of hydrazone compound used as a charge transport material represented by the following structural formula, and 10 pts. wt. of polycarbonate resin (manufactured by Teijin Kasei Co., Ltd.; trade name "Panlite TS-2050").

The mixture was then dissolved in 90 pts. wt. of tetrahydrofuran to obtain a plating for the charge transport layer. The amounts of the ester phosphite antioxidant and the hindered phenol antioxidant added (relative to the total solid quantity of the charge transport layer) were varied as shown in Table 1 below to obtain nine types of platings. After each of these platings was coated on the charge generation layer, the substrate was dried at 100 degrees C. for 20 minutes to form a charge transport layer about 20 μm in film thickness, thereby obtaining photoreceptors 1–1 to 1–9.

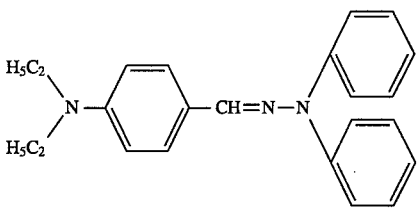

Each of these photoreceptors was evaluated for its photoreceptor characteristics and the respective amount that each resisted attack by ozone. The characteristics were evaluated using the static electricity charging test device EPA8100 manufactured by Kawaguchi Denki Seisakujo.

The surface of the photoreceptor was charged and initial charge potential $E_O$ was measured. The photoreceptor was subsequently exposed to white light at 5 lux in illuminance to determine half-decay exposure $E_{1/2}$ (sensitivity) required to decrease the initial charged potential to half. After the initial characteristics were measured in this manner, the photoreceptor was placed into a black box connected to an ozone generator to keep the concentration of ozone therein constant at 20 ppm. The photoreceptor was left in the ozone atmosphere for 11 hours.

The photoreceptor characteristics were subsequently measured as described above to determine a decrease in charged potential (%) due to

TABLE 1 wherein "Ester" denotes Ester phosphite, "phenol" denotes Hindered phenol & the decrease in charge potential is styled $E_0$ %.

| Photo-receptor No. | Content of Antioxidant (%) | | Photoreceptor characteristics | | | | |
|---|---|---|---|---|---|---|---|
| | | | Initial Stage | | After $O_3$ expos. | | |
| | Ester | Phenol | $V_0$ (V) | $E_{1/2}$ | $V_0$ (V) | $E_{1/2}$ | $E_0$ % |
| 1-3 | 0 | 0.5 | 592 | 4.0 | −527 | 3.8 | 11.0 |
| 1-2 | 0.5 | 0.5 | −598 | 4.2 | −564 | 4.1 | 5.7 |
| 1-3 | 1.2 | 0.5 | −609 | 4.5 | −587 | 4.2 | 3.6 |
| 1-4 | 2.4 | 0.5 | 615 | 4.1 | 595 | 4.1 | 3.3 |
| 1-5 | 4.7 | 1.5 | 626 | 4.3 | 617 | 4.4 | 1.4 |
| 1-6 | 2.4 | 0 | −597 | 4.0 | −552 | 3.9 | 7.5 |
| 1-7 | 2.4 | 0.2 | 602 | 4.0 | 582 | 4.0 | 3.3 |
| 1-8 | 2.4 | 1.0 | 623 | 4.7 | 606 | 4.7 | 2.7 |
| 1-9 | 0 | 0 | 581 | 3.8 | 414 | 3.5 | 28.7 |

Table 1 clearly shows that the addition of both the ester phosphite antioxidant and the hindered phenol antioxidant to a charge transport layer 3b provides a much higher degree of ozone proofness than when no such antioxidant is added or when only one of the antioxidants is added. The table also shows that the addition of both antioxidants improves charging characteristics without reducing sensitivity compared with the addition of only one of them.

EMBODIMENT 2

Photoreceptors 2–1 to 2–9 were prepared in the same manner as in Embodiment 1, except that the ester phosphite antioxidant and the hindered phenol antioxidant to be added to a charge transport layer were replaced with the component 2–1, (below in EXAMPLES section) that is, diphenylmono (2-ethylhexyl) phosphite and the component 4–2, (below in EXAMPLES section) that is, 2,5 bis (1,1,3,3-tetramethylbutyl)hydroquinone, respectively, and that the amount of each antioxidant added was changed as shown in Table 2. The characteristics and the ozone proof nature of these photoreceptors were evaluated as in Embodiment 1. Table 2 shows the results.

TABLE 2 wherein "Ester" denotes Ester phosphite, "phenol" denotes Hindered phenol & the decrease in charge potential is styled $E_0$ %.

| Photo-receptor No | Antioxident Cont. | | Photoreceptor characteristics | | | | $E_0$ % |
|---|---|---|---|---|---|---|---|
| | | | Initial Stage | | After $O_3$ expos. | | |
| | Ester | phenol | $V_0$ (V) | $E_{1/2}$ | $V_0$ (V) | $E_{1/2}$ | |
| 2-1 | 0 | 0.5 | −599 | 4.0 | −531 | 3.8 | 11.4 |
| 2-2 | 0.05 | 0.5 | −603 | 4.0 | −569 | 3.9 | 5.6 |
| 2-3 | 0.1 | 0.5 | −617 | 4.1 | −602 | 4.1 | 2.4 |
| 2-4 | 0.2 | 0.5 | −625 | 4.2 | 614 | 4.3 | 1.7 |
| 2-5 | 0.3 | 0.5 | −632 | 4.3 | 621 | 4.9 | 1.7 |
| 2-6 | 0.1 | 0 | −602 | 4.0 | −560 | 3.8 | 7.0 |
| 2-7 | 0.1 | 0.1 | −610 | 4.0 | 539 | 4.2 | 2.8 |
| 2-8 | 0.1 | 1.0 | −622 | 4.2 | 609 | 4.2 | 2.1 |
| 2-9 | 0 | 0 | −581 | 3.8 | 414 | 3.5 | 28.7 |

Table 2 shows that the addition of both the ester phosphite antioxidant and the hindered phenol antioxidant to a charge transport layer produces the same effects as in Embodiment 1.

EMBODIMENT 3

Photoreceptors 3-1 to 3-9 were prepared in the same manner as in Embodiment 1, except that the ester phosphite antioxidant and the hindered phenol antioxidant to be added to a charge transport layer were replaced with component 3-1, (below in EXAMPLES section) that is, tris (2-ethylhexyl) phosphite and the above component -3-, that is, pentaerythritol tetrakis [3-(3,5-di-t-butyl-4-hydrophenyl-)propionate], respectively, and that the amount of each antioxidant added was changed as shown in Table 3. The characteristics and the ozone proof nature of these photoreceptors were evaluated as in Embodiment 1. Table 3 shows the results.

TABLE 3 wherein "Ester" denotes Ester phosphite, "phenol" denotes Hindered phenol & the decrease in charge potential is styled $E_0$ %.

| Photo-receptor No. | Content of Antioxidant (%) | | Photoreceptor characteristics | | | | $E_0$ % |
|---|---|---|---|---|---|---|---|
| | | | Initial Stage | | After $O_3$ expos. | | |
| | Ester | Phenol | $V_0$ (V) | $E_{1/2}$ | $V_0$ (V) | $E_{1/2}$ | |
| 3-1 | 0 | 4.8 | 604 | 4.0 | 535 | 3.8 | 11.4 |
| 3-2 | 0.01 | 4.8 | −618 | 4.1 | 586 | 3.9 | 5.2 |
| 3-3 | 0.02 | 4.8 | −623 | 4.1 | 607 | 4.1 | 2.6 |
| 3-4 | 0.03 | 4.8 | −635 | 4.2 | −621 | 4.3 | 2.2 |
| 3-5 | 0.04 | 4.8 | −641 | 4.8 | −634 | 4.9 | 1.1 |
| 3-6 | 0.02 | 0 | −608 | 3.9 | 553 | 3.8 | 9.0 |
| 3-7 | 0.02 | 2.4 | −612 | 4.1 | −594 | 4.2 | 2.9 |
| 3-8 | 0.02 | 9.1 | −627 | 4.2 | −612 | 4.2 | 2.4 |
| 3-9 | 0 | 0 | −581 | 3.8 | −414 | 3.5 | 28.7 |

Table 3 shows that the addition of both the ester phosphite antioxidant and the hindered phenol antioxidant to a charge transport layer produces the same effects as in Embodiment 1.

It is therefore shown that improved results are produced by the photoreceptor of the present invention. This is because with an electrophotographic photoreceptor having a photosensitive bilayer of an organic material on a conductive substrate, wherein the outermost layer of said photosensitive layer contains both an ester phosphite antioxidant and a hindered phenol antioxidant improved properties are obtained. The formation of such a photosensitive bilayer provides an organic photoreceptor having improved durability against active gases such as ozone and enhanced repetition characteristics.

When the outermost layer of the photosensitive bilayer of a photoreceptor is a charge transport layer 3b, the following antioxidants should be added to the charge transport layer 3b. In this case, 0.001 to 10 wt. %, preferably 0.01 to 5 wt. % of an ester phosphite antioxidant and 0.01 to 10 wt. %, preferably 0.1 to 5 wt. % of a hindered phenol antioxidant relative to the total solid quantity of the charge transport layer should be added to this layer.

According to the present invention, such effects will not be produced when the amount of these antioxidants added is too small, while residual potential increases and sensitivity decreases when the amount of these antioxidants added is too large.

EXAMPLES

A preferred example of the ester phosphite antioxidant is a compound represented by the following general formula (1).

(1)

Wherein:

A represents a phenyl group that may have a substituent.

Specific examples of the compound represented by formula (1) include compounds represented by the following structural formulas (1)-1 to (1)-6.

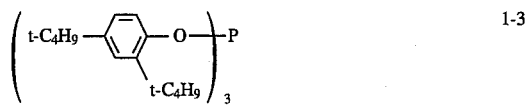

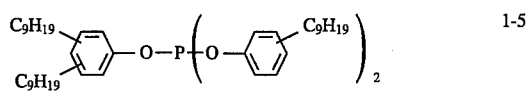

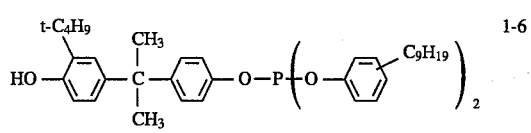

A preferred example of the ester phosphite antioxidant is a compound represented by the following general formula (2).

(2)

Wherein:

A represents a phenyl group that may have a substituent, $R_1$ represents an alkyl group with four carbon atoms or more.

Specific examples of the compound represented by formula (2) include compounds represented by the following structural formulas (2)–1 to (2)–4.

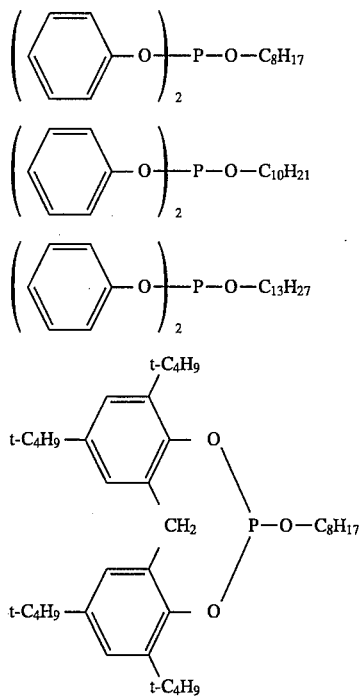

A preferred example of the ester phosphite antioxidant is a compound represented by the following general formula (3).

$$R_1-O-P-O-R_2 \atop |\atop O-R_3 \qquad (3)$$

Wherein:

A represents a phenyl group that may have a substituent.

$R_1$, $R_2$, and $R_3$ each represent an alkyl group with four carbon atoms or more.

Specific examples of the compound represented by formula (3) include compounds represented by the following structural formulas (3)–1 to (3)–5.

$(C_8H_{17}-O)_3P$     3-1

$(C_{10}H_{21}-O)_3P$     3-2

$(C_{13}H_{27}-O)_3P$     3-3

$(C_{18}H_{37}-O)_3P$     3-4

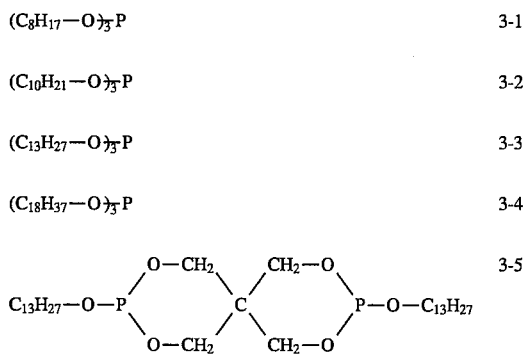

Specific examples of a hindered phenol antioxidant include compounds represented by the following structural formulas (4)–1 to (4)–10.

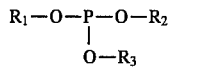

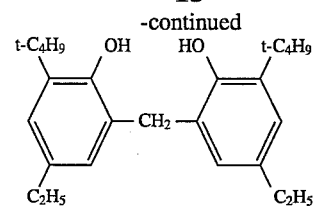

4-9

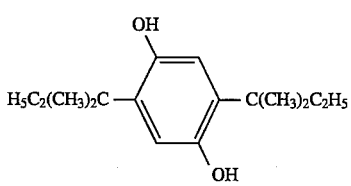

4-10

When a photosensitive bilayer comprises at least a charge generation layer 3a and a charge transport layer 3b formed in this order and said charge transport layer is the outermost layer, the charge transport layer should contain an ester phosphite antioxidant and a hindered phenol antioxidant.

According to the present invention, the charge transport layer preferably contains 0.001 to 10 wt. % of an ester phosphite antioxidant and 0.01 to 10 wt. % of a hindered phenol antioxidant, relative to the total solid quantity of the charge transport layer.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A negative-charge electrophotographic photoreceptor comprising:

a conductive substrate;

an intermediate layer on said conductive substrate;

a photosensitive bilayer of an organic material on said intermediate layer;

said photosensitive bilayer includes a charge generation layer and a charge transport layer;

said charge generation layer being deposited on said intermediate layer;

said charge transport layer being deposited on said charge generation layer;

said charge transport layer being an outermost layer of said photosensitive bilayer; and said charge transport layer contains an ester phosphite antioxidant and a hindered phenol antioxidant.

2. The negative-charge electrophotographic photoreceptor, as claimed in claim 1, wherein said ester phosphite antioxidant is a compound represented by a following general chemical formula:

[A—O]$_3$P wherein A represents a phenyl group that may have a substituent.

3. The negative-charge electrophotographic photoreceptor as claimed in claim 1, wherein said ester phosphite antioxidant is a compound represented by a following general chemical formula:

[A—O]$_2$P—O—R$_1$ wherein A represents a phenyl group that may have a substituent; and, $R_1$ represents an alkyl group with at least four carbon atoms.

4. The negative-charge electrophotographic photoreceptor as claimed in claim 1, wherein, said ester phosphite antioxidant is a compound represented by a following general formula:

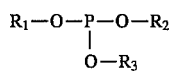

wherein $R_1$, $R_2$, and $R_3$ each represent an alkyl group with four carbon atoms or more.

5. The negative-charge electrophotographic photoreceptor as claimed in claim 1, wherein said intermediate layer is one member selected from the group consisting of polyvinyl alcohol, polyvinyl methyl ether, polyamide, polyurethane, melamine resin, phenol resin, and aluminum oxide.

6. The negative-charge electrophotographic photoreceptor as claimed in claim 1, wherein said charge transport layer contains 0.01 to 10 wt. % of an ester phosphite antioxidant and 0.01 to 10 wt. % of a hindered phenol antioxidant, relative to the total solid quantity of the charge transport layer.

7. A negative-charge electrophotographic photoreceptor comprising:

a conductive substrate;

an intermediate layer on said substrate;

a photosensitive bilayer of an organic material on said intermediate layer;

an outermost layer of said photosensitive bilayer contains an ester phosphite antioxidant and a hindered phenol antioxidant; and said ester phosphite antioxidant is a compound represented by a following general chemical formula:

[A—O]$_3$P wherein A represents a phenyl group that may have a substituent.

8. A negative-charge electrophotographic photoreceptor comprising:

a conductive substrate;

an intermediate layer on said substrate;

a photosensitive bilayer of an organic material on said intermediate layer;

an outermost layer of said photosensitive bilayer contains an ester phosphite antioxidant and a hindered phenol antioxidant; and said ester phosphite antioxidant is a compound represented by a following general chemical formula: said ester phosphite antioxidant is at least one compound selected from the group represented by the following general chemical formulas:

[A—O]$_2$P—R$_1$ wherein A represents a phenyl group that may have a substituent, $R_1$ represents an alkyl group with four carbon atoms or more, and

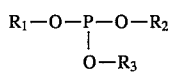

wherein $R_1$, $R_2$, and $R_3$ each represent an alkyl group with four carbon atoms or more.

9. A method for producing a negative-charge electrophotographic photoreceptor comprising:

coating an intermediate layer on a conductive substrate;

coating a charge generation layer on said intermediate layer;

preparing a solution containing a hindered phenol and an ester phosphite anti-oxidant; and coating said solution on said charge generation layer to form a charge transport layer.

* * * * *

UNITED STATES PATENT AND TRADEMARK OFFICE
CERTIFICATE OF CORRECTION

PATENT NO. : 5,567,557  Page 1 of 2
DATED : October 22, 1996
INVENTOR(S) : Nobuyoshi MORI It is certified that an error appears in the above-identified patent and that said Letters Patent is hereby corrected as shown below:

Cover Page, Abstract, line 4, replace "layer if" with --layer of--.

Column 3, line 2, after "in" delete comma.

Column 4, line 2, replace "electrophotgraphic" with --electrophotographic--;

line 3, after "prises" delete semicolon;

line 14, replace "electrophotgraphic" with --electrophotographic--;

line 15, after "prises" delete semicolon;

line 27, after "prises" delete semicolon;

line 44, after "comprises" delete semicolon;

line 56, delete "and";

line 58, replace "more." with --more, and--.

Column 5, line 1, after "comprising" delete semicolon;

line 29, replace "pans" with --parts--;

line 43, replace "examle" with --example--.

Column 6, line 2, after "polyvinyl" delete period.

UNITED STATES PATENT AND TRADEMARK OFFICE
CERTIFICATE OF CORRECTION

PATENT NO. : 5,567,557

DATED : October 22, 1996

INVENTOR(S) : Nobuyoshi MORI

It is certified that an error appears in the above-identified patent and that said Letters Patent is hereby corrected as shown below:

Column 9, Table 2, under "Photoreceptor characteristics" replace "Antioxident" with --Antioxidant--;

Table 2, under "Photoreceptor characteristics Initial Stage, replace "$E/_{1,2}$" with --$E_{1/2}$--;

line 33, replace "component -3-," with --component 4-3,--.

Signed and Sealed this

Sixteenth Day of September, 1997

Attest:

BRUCE LEHMAN

*Attesting Officer*   *Commissioner of Patents and Trademarks*